(12) United States Patent
Bendtsen et al.

(10) Patent No.: US 7,829,339 B2
(45) Date of Patent: Nov. 9, 2010

(54) METHOD FOR CASEIN DETERMINATION IN MILK

(75) Inventors: Anders Broe Bendtsen, Virum (DK); Poul Erik Petersen, Valby (DK)

(73) Assignee: Foss Analytical A/S, Hillerod (DK)

( * ) Notice: Subject to any disclaimer, the term of this patent is extended or adjusted under 35 U.S.C. 154(b) by 0 days.

(21) Appl. No.: 12/705,889

(22) Filed: Feb. 15, 2010

(65) Prior Publication Data

US 2010/0176299 A1    Jul. 15, 2010

Related U.S. Application Data

(62) Division of application No. 10/503,978, filed as application No. PCT/DK03/00085 on Feb. 10, 2003, now Pat. No. 7,704,744.

(30) Foreign Application Priority Data

Feb. 11, 2002    (DK) ............................... 2002 00203

(51) Int. Cl.
G01N 33/04    (2006.01)
(52) U.S. Cl. .................. 436/22; 436/23; 422/82.05; 422/82.09
(58) Field of Classification Search .............. 436/22, 436/23; 422/82.05, 82.09
See application file for complete search history.

(56) References Cited

U.S. PATENT DOCUMENTS 5,983,709 A    11/1999    O'Keeffe 6,174,729 B1    1/2001    Alam
6,297,505 B1    10/2001    Frandsen et al.

FOREIGN PATENT DOCUMENTS

WO    WO 81/02467    3/1981

OTHER PUBLICATIONS

Notice of Allowance U.S. Appl. No. 10/503,978 dated Nov. 16, 2009.
Final Office Action U.S. Appl. No. 10/503,978 dated Jul. 6, 2009.
Non-Final Office Action U.S. Appl. No. 10/503,978 dated Dec. 19, 2008.
Non-Final Office Action U.S. Appl. No. 10/503,978 dated Jun. 11, 2008.

(Continued)

Primary Examiner—Robert J Hill, Jr.
Assistant Examiner—Dwan A Gerido
(74) Attorney, Agent, or Firm—Stephen A. Bent; Foley & Lardner LLP (57) ABSTRACT

The content of casein in milk is determined by two measurements of infrared absorbance in a milk sample by infrared spectrometry before and after a separation of the casein. The casein content is calculated by use of absorbance data recorded during the two absorbance measurements. The new method is considerable faster than the known wet-chemical methods, such as the normal wet chemical reference method for casein determination in milk using a Kjeldahl nitrogen determination of the milk sample, then a coagulation of the milk, and finally a Kjeldahl nitrogen determination of the filtrate. Further the new method provides a more reliable accuracy than the know determination using a single infrared analysis of a milk sample.

6 Claims, 7 Drawing Sheets

OTHER PUBLICATIONS

D.M. Barbano & M.E. Dellavalle, Journal of Dairy Science 70:1524-1528, 1987.

International Search Report, Apr. 29, 2003.

A.H. Karman et al., "A simple and rapid method to determine the casein content of milk by infrared spectrophotometry", Neth. Milk Dairy J., vol. 41, 1987, pp. 175-187.

D.M. Barbano et al., "Rapid Method for Determination of Milk Casein Content by IR Analysis", Journal of Dairy Science, vol. 70, No. 8, 1987, pp. 1524-1528.

F. Taha et al., "Routine determination of protein and casein content of milk by infrared (IR) method", Mitteilungen Aus Dem Gebiete Der Lebensmitteluntersuchung Und Hygiene, vol. 84, No. 1, 1993, pp. 122-140.

Database STN International [Online] File CAPLUS, document nr 121:253959; retrieved from CAPLUS, Database accession No. 1994:653959 XP002239646 *abstract -& R. Grappin et al., "5.1 reference and routine methods for measurement of nitrogen fractions in milk and whey", International Dairy Federation, Special Issue 1994, pp. 191-203.

Luginbuhl Werner, "Evaluation of designed calibration samples for casein calibration in fourier transform infrared analysis of milk", Lebensmittel-Wissenschaft & Technologie, vol. 35, No. 6, 2002, pp. 554-558.

METHOD FOR CASEIN DETERMINATION IN MILK

CROSS-REFERENCE TO RELATED PATENT APPLICATIONS

This application is a Divisional Application of U.S. Ser. No. 10/503,978 filed May 2, 2005 which is the U.S. National Stage of PCT/DK03/00085 filed Feb. 10, 2003, which claims priority from Denmark Application No. PA 2002 00203 filed Feb. 11, 2002, each of which is incorporated herein by reference in its entirety.

TECHNICAL FIELD

The present invention concerns a method for casein determination in milk and instruments enabled to carry out the method.

BACKGROUND

Milk contains proteins such as caseins. The caseins are specifically useful for cheese-making, due to their ability to coagulate. Accordingly chemical methods for determining the content of casein in milk are known. They are however time consuming. Further, It is known to determine the casein content in milk directly by fast infrared analysis methods. However, the accuracy of these methods depends on the match between the calibration samples applied for the calibration of the infrared analysis instrument and the routine samples for which the content of casein is to be determined.

The purpose of the present invention is to propose a method, which is more universal, such as independent of the origin of calibration samples, than the known infrared analysis.

In the present description the word "milk" relates to the milk sample to be analysed. The words "liquid phase" and supernatant are used for the remaining portion of the milk sample after a separation of the casein. The supernatant contains whey-protein.

Supernatant is in this description intended also to address the case when the liquid phase in fact is a filtrate.

THE INVENTION

The present invention concerns a method for determination of the content of casein in milk, wherein a milk sample is measured before and after a separation into casein and a liquid phase, called a supernatant. According to the invention the protein content is determined by measuring the infrared absorbance in the milk sample before separation by infrared spectrometry and, measuring the infrared absorbance in the supernatant (liquid phase of the milk sample after separation of casein) by infrared spectrometry, and calculating the casein content by use of absorbance data recorded during the two infrared spectrometry measurements of absorbance.

Preferably and according to the invention the separation of casein is promoted by adding at least one chemical solution, adequate for precipitation of casein, to the milk sample, and a dilution factor (Df) indicating the dilution of the supernatant compared to the original milk sample is calculated and applied for the calculation of the concentration of casein.

Preferably and according to the invention the concentration of protein, (P (Milk)) in the milk sample before separation is determined from the infrared absorbance in the milk sample before separation, and the concentration of protein, (P (SN)) in the supernatant is determined from the infrared absorbance in supernatant, and the concentration of casein is calculated as the difference between the concentration of protein (P (Milk)) in the milk sample and the dilution factor (Df) multiplied by the concentration of protein (P (SN)) in the supernatant as defined by the equation:

$$P(\text{Casein}) = P(\text{Milk}) - (Df * P(SN))$$

In the present description P (Milk) means the concentration of total proteins measured in a milk sample. The total protein is a combination of caseins and whey-proteins. The whey-protein does not precipitate; it remains fluent in the supernatant. P (Whey) means the concentration of whey-protein in a milk sample, and P (SN) means the concentration of whey-protein measured in the supernatant. The dilution factor is important because the addition of chemicals to obtain the precipitation of casein causes a dilution of the sample.

Accordingly the measured P (SN) is lower than the P (Whey) due to the dilution.

Preferably and according to the invention the method is characterised by comprising the steps 1) a fraction of a milk sample is analysed by mid-infrared spectroscopy to determine the content of protein, P (Milk),
2) an acid, initiating a precipitation of casein, is added to a remaining fraction of the milk sample and mixed with the sample,
3) a salt of the acid is added to obtain a pH about 4.6 and the sample is mixed again
4) the fluid mixture is subjected to a separation process separating the fluid mixture into a liquid phase, called the supernatant, and a precipitate of casein,
5) the supernatant is transferred into a container, and a sample of the supernatant is analysed by mid-infrared spectroscopy to determine the content of protein in the supernatant, P (SN)
6) the content of whey-protein, P (Whey) in the original milk sample is calculated from the content of protein in the supernatant (liquid phase) by incorporating the dilution of the supernatant, caused by the addition of acid and salt,
7) the casein content in the original milk sample is calculated as:

$$\text{Content of casein} = P(\text{Milk}) - P(\text{Whey}).$$

The separation may be carried out by adding an acid initiating a precipitation of casein, preferably adding a salt of the acid maintaining a pH supporting the precipitation of casein, mixing or stirring the mixture, centrifuging the mixture, and collecting the liquid phase, also called the supernatant in a receptacle.

Preferably the separation comprises a filtration. A filtration is advantageous, as the infrared spectrometric instruments generally require samples without particles bigger than about 20 um. Preferably the separation comprises a centrifugation. Preferably the acid is acetic acid. Preferably the salt is sodium acetate. These chemicals promote effectively a precipitation of the casein.

The method may be carried out by use of spectroscopic infrared analysis instrument having a plurality of infrared filters enabling an accurate determination of the protein content in a milk sample. Preferably the instrument further includes one or more filters enabling a correction or compensation taking account of the added chemicals, such as acid and salt, in order to ensure that the accuracy of the protein determination is not considerably deteriorated by the presence of the added chemicals.

More preferably the method is carried out by use of a full spectrum instrument arranged for recording a spectrum substantially comprising the spectral range from about 1000-3000 cm$^{-1}$, such as a MilkoScan FT120.

Preferably the method is carried out by use of a full spectrum instrument, having a first protein calibration enabling a calculation of the protein content from the spectrum of the milk. The full spectrum instrument with adequate calibrations is preferred in order to ensure enabling of an accurate determination of the protein content in a milk sample, the accuracy not being substantially deteriorated by the presence of the added chemicals.

This specification does not include an example disclosing a calibration as such calibrations are highly dependent on the type of instrument and further may depend on local environmental conditions. However, it is a well-known fact that such calibrations may be provided in many ways by people skilled in the art of multivariate calibration of spectrometric instruments.

Preferably the method is carried out by use of a full spectrum instrument having a "dilution" calibration enabling a calculation of the dilution factor from the spectrum of the supernatant-sample. Preferably the method is carried out by use of a full spectrum instrument having a second protein calibration enabling a calculation of the protein content from the spectrum of the supernatant-sample (also called the filtrate).

Preferably the protein calibration for the supernatant sample is robust to variations in the concentrations (different additions) of acetic acid/sodium acetate.

According to the present invention a preferred method for determination of casein in milk is proposed, comprising the following steps:
1) a fraction of a milk sample is analysed by mid-infrared spectroscopy to determine the content of protein, P (Milk),
2) acetic acid is added to a remaining fraction of the milk sample and mixed with the sample so that a precipitation of casein is initiated,
3) sodium acetate is added to obtain a pH about 4.6 and the sample is mixed again
4) the fluid mixture is centrifuged,
5) the supernatant is transferred into a receptacle, such as a new bottle or flask, and the resulting supernatant sample is analysed by MiD-infrared spectroscopy to determine the content of protein, P (SN),
6) a dilution factor is calculated,
7) the whey-protein is calculated as P (Whey)=P (SN)*dilution factor, 8) the casein content in the milk is calculated as Content of casein=P (Milk)–P (Whey).

The new method is considerable faster than the known chemical methods, such as the normal wet chemical reference method for casein determination in milk using a Kjeldahl nitrogen determination of the milk sample, then a coagulation of the milk, and finally a Kjeldahl nitrogen determination of the filtrate. Further the new method provides a more reliable accuracy than the know determination using a single infrared analysis of a milk sample.

Preferably, the mid-infrared spectroscopy is carried out by use of a full spectrum instrument, such as a MilkoScan FT120 in order to obtain recorded spectral data comprising sufficient information. Preferably the recorded spectrum includes the spectral range from about 1000-3000 cm~1 or at least substantial wavebands thereof. Preferably, the full spectrum instrument includes data processing means for analysing the spectral data.

Preferably, the full spectrum instrument comprises a protein calibration enabling a calculation of the protein content from the spectral data representing the spectrum of the milk. Advantageously, the full spectrum instrument may be arranged to calculate the protein content almost immediately to provide a rapid result. Alternatively the spectral data might be transferred to remote data processing means arranged to perform a calculation of the protein content from the spectrum of the milk.

Preferably, the full spectrum instrument also comprises a further protein calibration, also called a whey-protein calibration, enabling a calculation of the whey-protein content from the spectrum of the supernatant-sample (also called the filtrate or the whey).

Advantageously, the full spectrum instrument may be arranged to calculate the protein content all most immediately to provide a rapid result.

Alternatively the spectral data might be transferred to remote data processing means arranged to perform a calculation of the protein content from the spectrum of the supernatant.

The dilution factor may be calculated from weight results measured by a scale or from volumetric determinations. Accordingly, the casein content may be determined from the two recorded spectra and the calculated dilution factor: P (Milk)–P (SN)*dilution factor.

Alternatively and preferably, the full spectrum instrument comprises a "dilution factor" calibration enabling a calculation of the dilution factor from the spectral data representing the spectrum of the supernatant-sample. Experience has proved that calculation of a dilution factor from the spectrum of the supernatant sample may improve the accuracy of the measurement. Also this feature supports rapid provision of a result. Accordingly, the casein content may be determined from the two recorded spectra and the dilution factor calculated from the spectrum: P (Milk)–P (SN)*dilution factor.

Preferably, the whey-protein calibration for the supernatant sample is robust to variations in the concentrations (different additions) of acetic acid/sodium acetate. This feature is advantageous in that it will compensate for variation in the amount of added acetic acid/sodium acetate. Such variations are unavoidable in the practical life.

According to a further alternative method, the whey-protein may be determined directly from the spectroscopy using a single calibration, enabling the calculation of whey-protein in milk from the spectral data representing the spectrum of the supernatant (also called the whey sample). Accordingly, this single calibration may replace the above"whey-protein in supernatant"-calibration and the"dilution"-calibration for calculation of the "dilution factor". Such single calibration is preferably a calibration incorporating the dilution factor, i.e. a calibration providing the same result for P (whey) as the result obtained from the calculation P (SN)*dilution factor, when using the two separate calibrations for the supernatant (also called the whey).

Among the advantages of the methods according to the present invention is that the methods may be carried out on a great number of instruments already located in laboratories all over the world. A further advantage is that a method according to the invention is more accurate than the known methods.

Further the present invention relates to a mid IR spectrometric analysis instrument characterized in that the instrument comprises a software program enabling an execution of the calculations involved in a method for the determination of the content of casein according to any of the preceding claims by use of data recorded by the mid IR spectrometric analysis instrument.

In a preferred embodiment the mid IR spectrometric analysis instrument is characterized in that the instrument comprises a software program enabling an execution of the calculations of the content of casein by use of data enabling a calculation of a dilution factor indicating the dilution of the whey compared to the original milk sample.

In a preferred embodiment the mid IR spectrometric analysis instrument is characterized in that the instrument comprises a software program enabling an execution of a method, the instrument having a second protein calibration enabling a calculation of the protein content from the spectrum of the supernatant-sample (also called the filtrate).

In a preferred embodiment the mid IR spectrometric analysis instrument is characterized in that the instrument comprises a software program enabling an execution of the method according to any of the method claims, and wherein the spectrometric instrument comprises a plurality of interchangeable optical IR filters able to be inserted into the light path of the spectrometric instrument as known per se.

In a preferred embodiment the mid IR spectrometric analysis instrument is characterized in that the instrument comprises a software program enabling an execution of a method according to the invention and wherein the spectrometric instrument is a Full spectrum instrument providing data representing a substantial portion of the MID-IR spectrum.

In a preferred embodiment the mid IR spectrometric analysis instrument is characterized in that the instrument comprises a software program enabling an execution of a method according to any of the method claims and wherein the spectrometric instrument provides data representing substantial portions of the MID-IR wavebands wherein proteins absorb and/or wherein the added acid and/or salt absorb.

The use of a full spectrum instrument, such as a FTIR instrument is specifically advantageous as the data of the full spectrum allow for a good compensation of the influence from the added acetic acid. However, a mid IR instrument having a plurality of filters may also be applied for executing the method according to the invention.

DETAILED DESCRIPTION OF THE INVENTION

Figure 1:
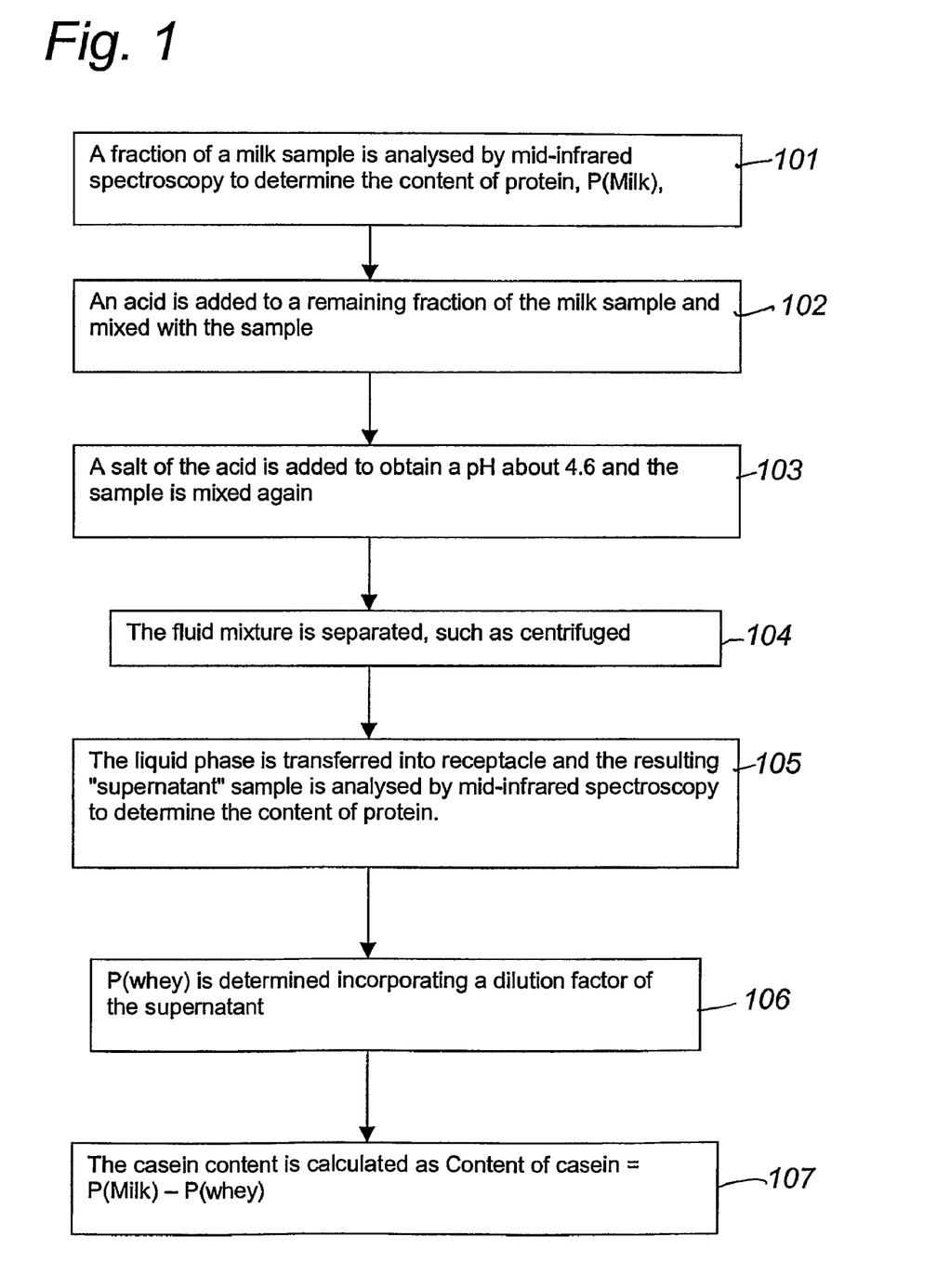
FIG. 1 shows a flow diagram illustrating the broadest aspect of the method according to the invention.

FIG. 1 illustrates the broadest aspect of the invention. A fraction of a milk sample is analysed by mid-infrared spectrometry in step 101. The content of protein, P (milk), is determined from the spectral data by use of well-known chemometric methods for quantitative determinations. An acid of known concentration/strength able to precipitate casein is added to a remaining fraction of the milk sample, and mixed with the sample in step 102. A salt of the acid of known concentration is added to obtain a stable pH, such as about 4.6, and the sample is mixed again to complete the precipitation of casein in step 103. The fluid mixture is separated into a liquid phase called the supernatant and a precipitate of casein, preferably by centrifugation and/or by filtration in step 104.

The supernatant is then transferred to a container, such as a receptacle and a sample of the supernatant (or filtrate) is analysed by mid-infrared spectrometry in step 105. A dilution factor accounting for the dilution in the supernatant compared to the milk sample is calculated. The dilution is due to the addition of acid and salt in order obtain the precipitation. The content of protein P (whey) is determined from the spectral data and the dilution factor in step 106.

The casein content in the original milk sample may then be calculated as P (milk)–P (whey) as indicated in step 107.

EXAMPLE OF A PREFERRED METHOD

Figure 2:
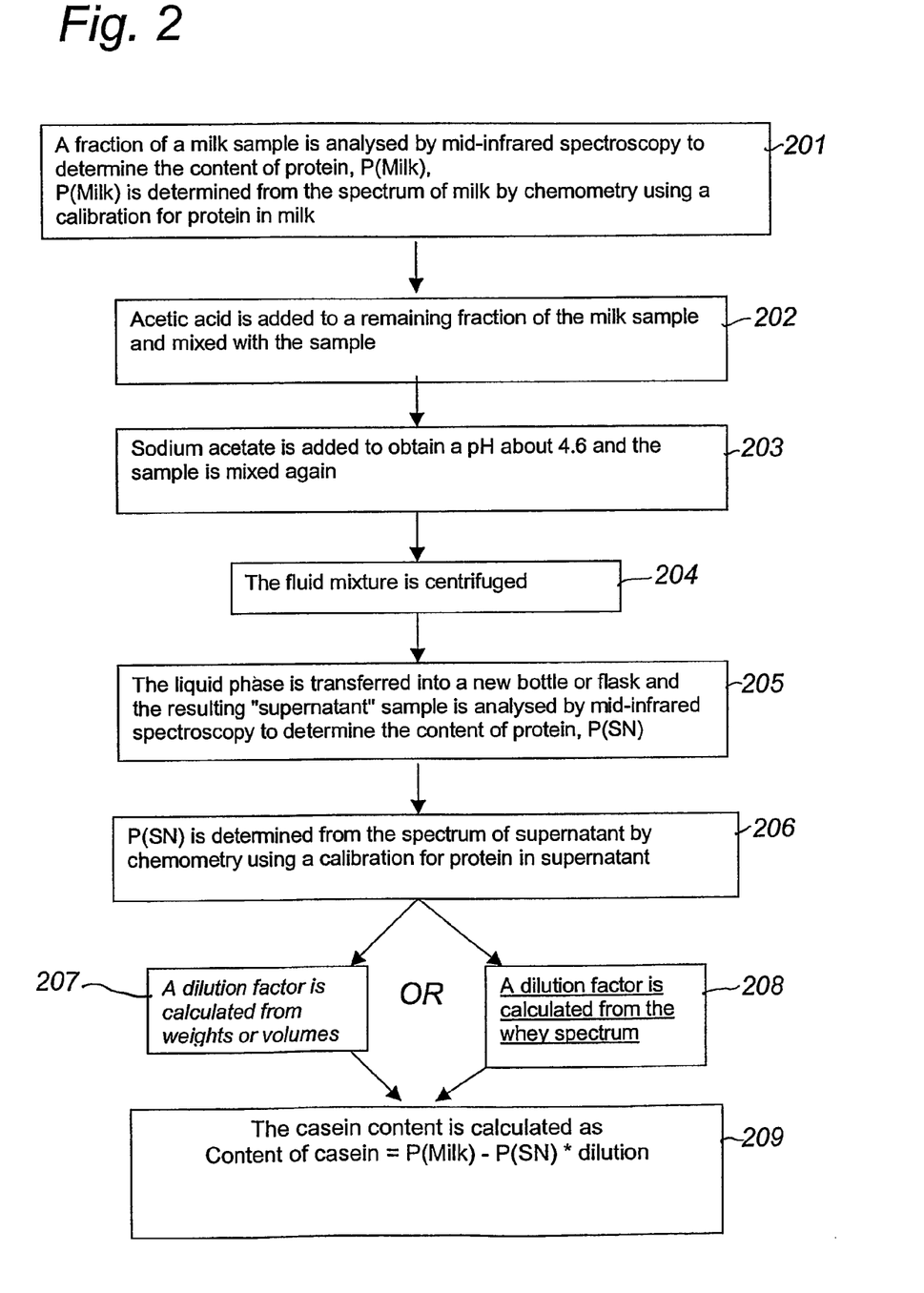
FIG. 2 shows a flow diagram illustrating a preferred method according to the invention.

FIG. 2 illustrates a preferred method using acetic acid and sodium acetate for the precipitation of the casein. In step 201 a fraction of a milk sample is analysed by mid-infrared spectroscopy to determine the content of protein, P (Milk), P (Milk) is determined from the spectrum of milk by chemometry using a calibration for protein in milk. In step 202 Acetic acid is added to a remaining fraction of the milk sample and mixed with the sample. In step 203 Sodium acetate is added to obtain a pH about 4.6 and the sample is mixed again. In step 204 The fluid mixture is centrifuged. In step 205 the supernatant is transferred into a new container, such as a bottle or flask and the resulting "supernatant" sample is analysed by mid-infrared spectroscopy to determine the content of protein, P (SN). In step 206 P (SN) is determined from the spectrum of supernatant by chemometry using a calibration for protein in supernatant.

The next steps 207 and 208 are alternative. The dilution factor has to be found. The dilution factor may e.g. be calculated from measured weights or volumes (step 207) or from the whey spectrum using a chemometric method (step 208).

In step 209 the casein content is calculated as

Content of casein=$P$(Milk)–$P$(SN)*dilution

Figure 3:
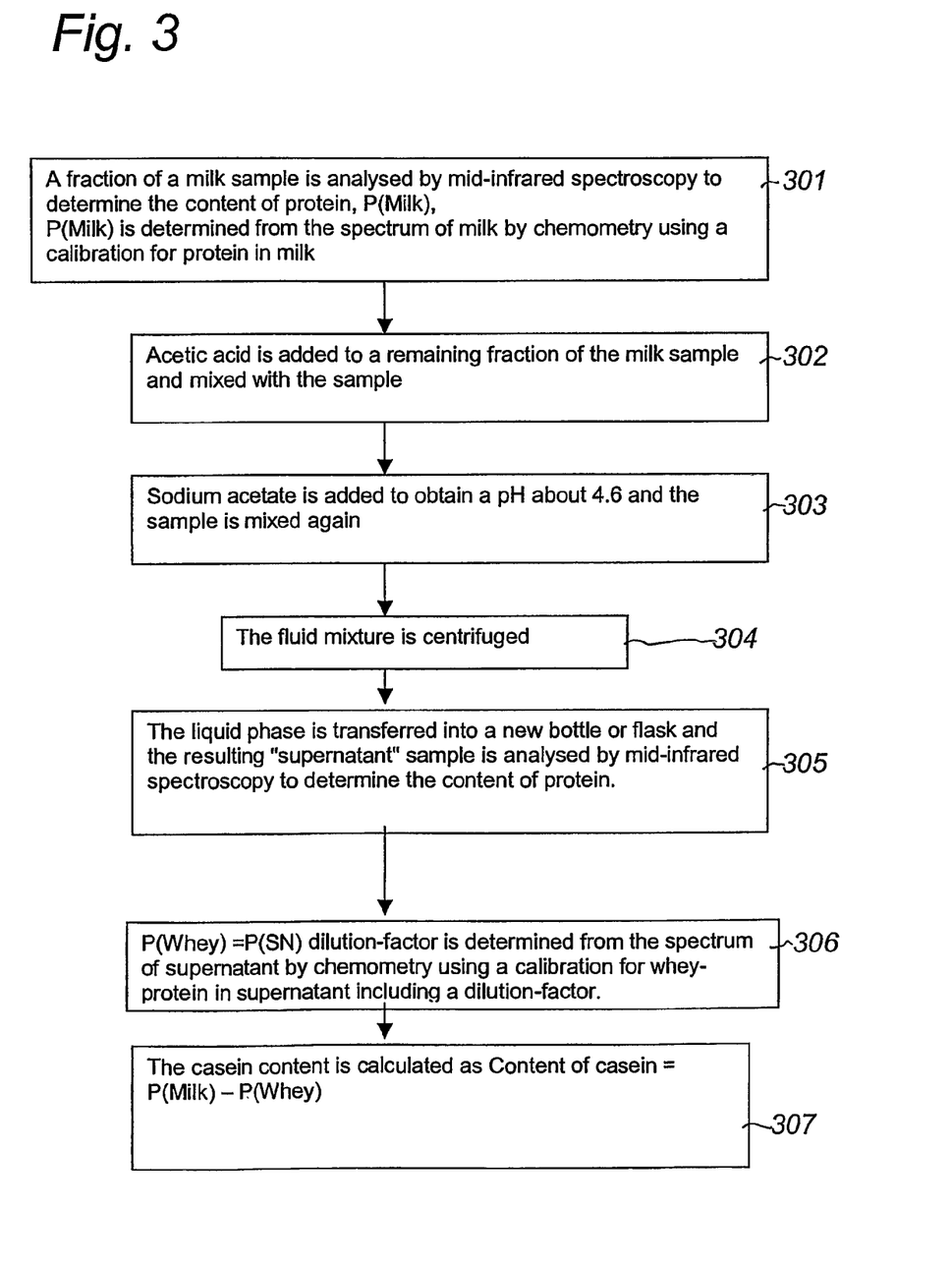
FIG. 3 shows a flow diagram illustrating an alternative method according to the invention.

FIG. 3 shows a procedure very similar to FIG. 2. In fact the steps 301-305 are identical to steps 201-205. The next step 306 will be explained in further details later in this description.

According to the invention the following fast differential infrared method for casein determination is recommended.

Instrumentation

The method may be carried out by use of a mid-IR spectrometer, preferably a MilkoScan FT120 from FOSS Electric A/S. In the following text the abbreviation MScFT120 is used. The preferred instrument is a full spectrum instrument, such as MScFT120, able to record at least essential portions of a mid IR spectrum. However, as an alternative a spectrometric instrument, such as the Milkoscan 4000, using a plurality of filters enabling a good determination (prediction) of the content protein in milk, may also be used.

Chemicals
1. 10% Acetic Acid
2. 1. OM (mol/liter) sodium acetate

Procedure

The milk sample should have a temperature about 20-38 degree (Celsius). The milk may be preserved.

Measure the undiluted milk sample by MScFT120
Determination of the protein content of the milk
Sample 100 ml (or 100 g) of the milk'

Add 20 ml (or 20 g) of the 10% acetic acid. Mix the sample.
'Add 20 m) (or 20 g) of the 1. OM sodium acetate. Mix the sample.
Centrifuge the sample using minimum 10500 rpm in 5 min. or until separation between supernatant and precipitate looks fine. The supernatant do not have to look clear.
The supernatant is carefully poured into a test tube through a filter. Some of the precipitate may break up. The filter will prevent that it pollutes the filtrate.
Therefore it may be a fast filter (e.g. a mechanical filter).
Measure the supernatant (the filtrate) by MScFT120.
Determination of the Protein content in the filtrate and the dilution factor.

The added amount of acetic acid may vary. Preferably an amount of no less than 10 ml 10% acetic acid for 100 ml milk sample is applied in order to obtain the desired precipitation. It is not recommended to add more than about 30 ml, as the dilution increases and deteriorate the spectrum. The concentration of the acetic acid and the sodium acetate must be very accurate when using the dilution calibration to determine the dilution factor.

Alternatively a buffer solution is added directly to the milk in one step to obtain the precipitation.

IR Calibrations

The casein content in the sample is determined by 3 different IR calibrations stored in the MScFT120.
1) Protein calibration for milk
2) Whey-protein calibration for the supernatant (filtrate)
3) Dilution factor calibration Although addition of acetic acid results in high absorbancies in the same region as protein, this makes no problems for the protein determination using a full-spectrum IR instrument.

Therefore the combination of the recommended procedure with this kind of instrument is recommended. The protein calibration for the filtrate may be made robust for various concentrations (different additions) of acetic acid/sodium acetate.

The calibration for the dilution factor is also a new feature in the system allowing an inaccurate addition of the acetic acid and the sodium acetate. This, however, assumes that the concentrations of the chemicals are accurate. The prediction of the dilution factor from the spectrum (mentioned in FIG. 2 step 208) replaces the weight results from a scale or replaces a volume determination.

Advantageously, and as indicated in step 306 in FIG. 3, the last two calibrations may be combined into a single calibration. However, where a more flexible system is wanted it may be preferred to have the two separate calibrations, as shown in FIG. 2 step 207, 208, thereby providing a possibility to choose between the weight results or the dilution factor calibration.

Figure 4:
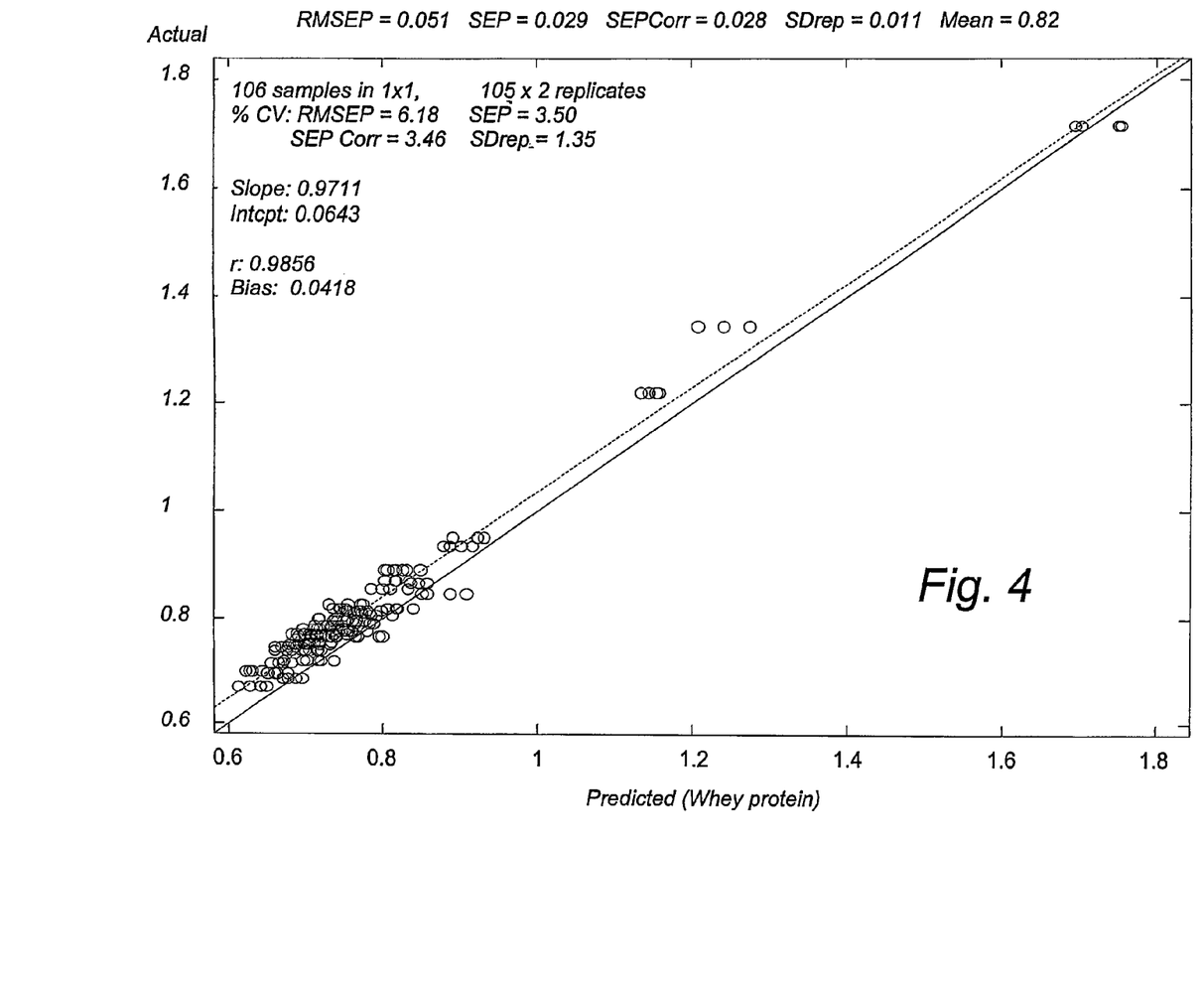
FIG. 4 shows a prediction plot for whey-protein in milk corresponding to the predicted protein in the filtrate times the dilution factor calculated by weight results (approximately 1.4).

FIG. 4 shows prediction of the whey protein in a plurality of milk samples.
Number of samples: 106 samples in 1×1, 105×2 replicates
The obtained absolute accuracy is:
RMSEP=0.051; SEP=0.029; SEPCorr=0.028; SDrep=0.011; Mean=0.82.
The accuracy relative to the mean is: RMSEP=6.18% CV; SEP=3.50% CV; SEPCorr=3.46% CV; SDrep=1.35% CV.
Slope: 0.9711; Intercept: 0.0643; correlation coefficient r: 0.9856; Bias: 0.0418.
In this context RMSEP is the "root mean square" of Error of Prediction.
SEP is the Standard Error of Prediction.
SEPCorr is the slope-and intercept-corrected SEP.

SDrep is the standard deviation of the repeatability.
Mean is the mean value of the constituent (content of proteins, whey or casein).
Correlation coefficient: r The content of whey-protein is determined as predicted protein in the supernatant multiplied by a dilution factor. This dilution factor can be calculated from the weight results or it can be determined by prediction too. In FIG. 4 the weight results are used to calculate the dilution factor.

Figure 5:
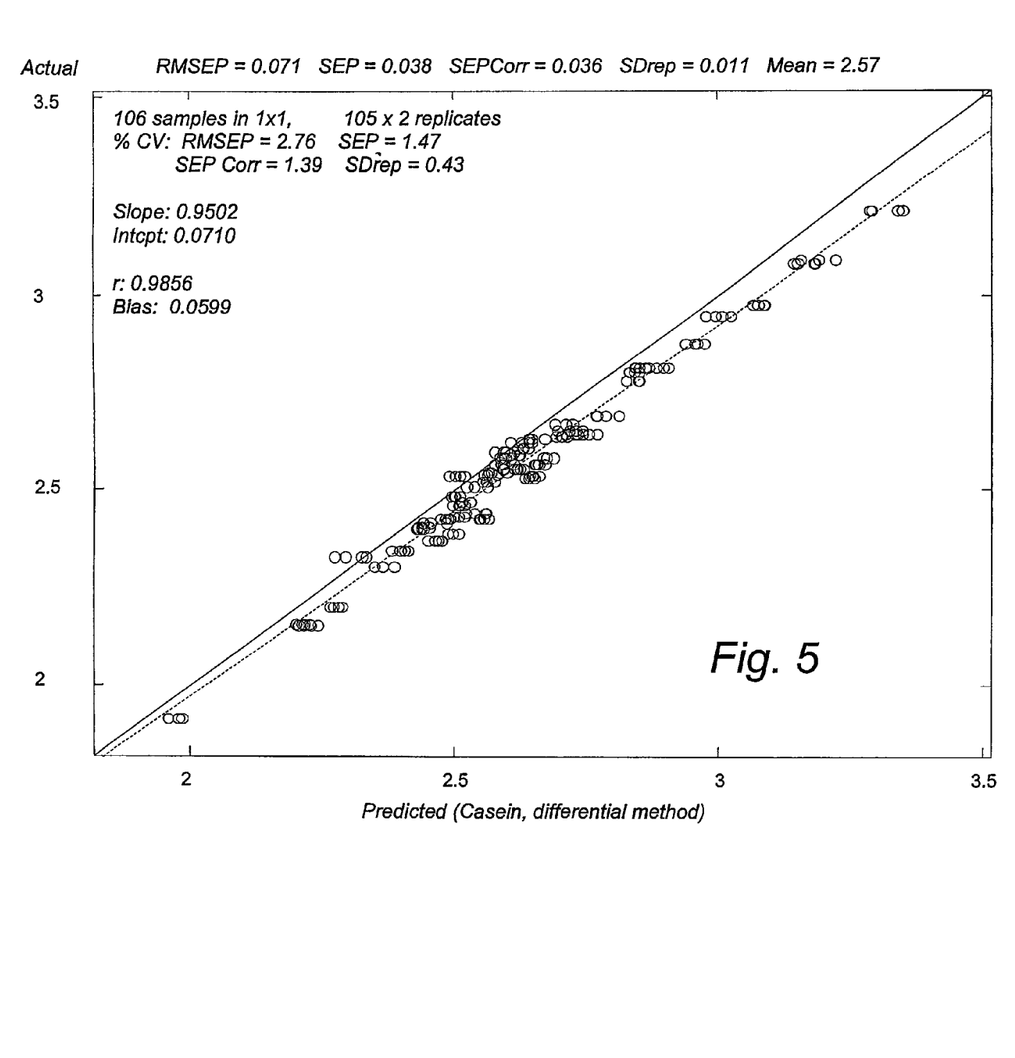
FIG. 5 shows a resulting prediction plot for the differential casein determination using the weight results to calculate the dilution factor.

The predicted casein content is calculated as:

$$Casein = Pm - Pf * Df$$

where
Pm=Predicted protein in milk
Pf=Predicted protein in the supernatant of the corresponding milk
Df=Dilution factor The reference casein versus predicted casein by the method according to the invention is presented in a prediction plot in FIG. 5 (using the weight results for calculation of the Df).

The FIG. 5 plot relates to the same samples as FIG. 4:
Number of samples: 106 samples in 1×1, 105×2 replicates
The obtained absolute accuracy is:
RMSEP=0.071; SEP=0.038; SEPCorr=0.036; SDrep=0.011; Mean=2.57.
The accuracy relative to the mean is: RMSEP=2.76% CV; SEP=1.47% CV; SEPCorr=1.39% CV; SDrep=0.43% CV.
Slope: 0.9502; Intcpt: 0.0710; r: 0.9856; Bias: 0.0599

According to a known method, a so-called "multiplication method" the casein content may be determined as approximately equal to the protein content multiplied by 0.76. A prediction plot resulting from the use of this multiplication method is presented in FIG. 6 for comparison with the new method as presented in FIG. 5.

Figure 6:
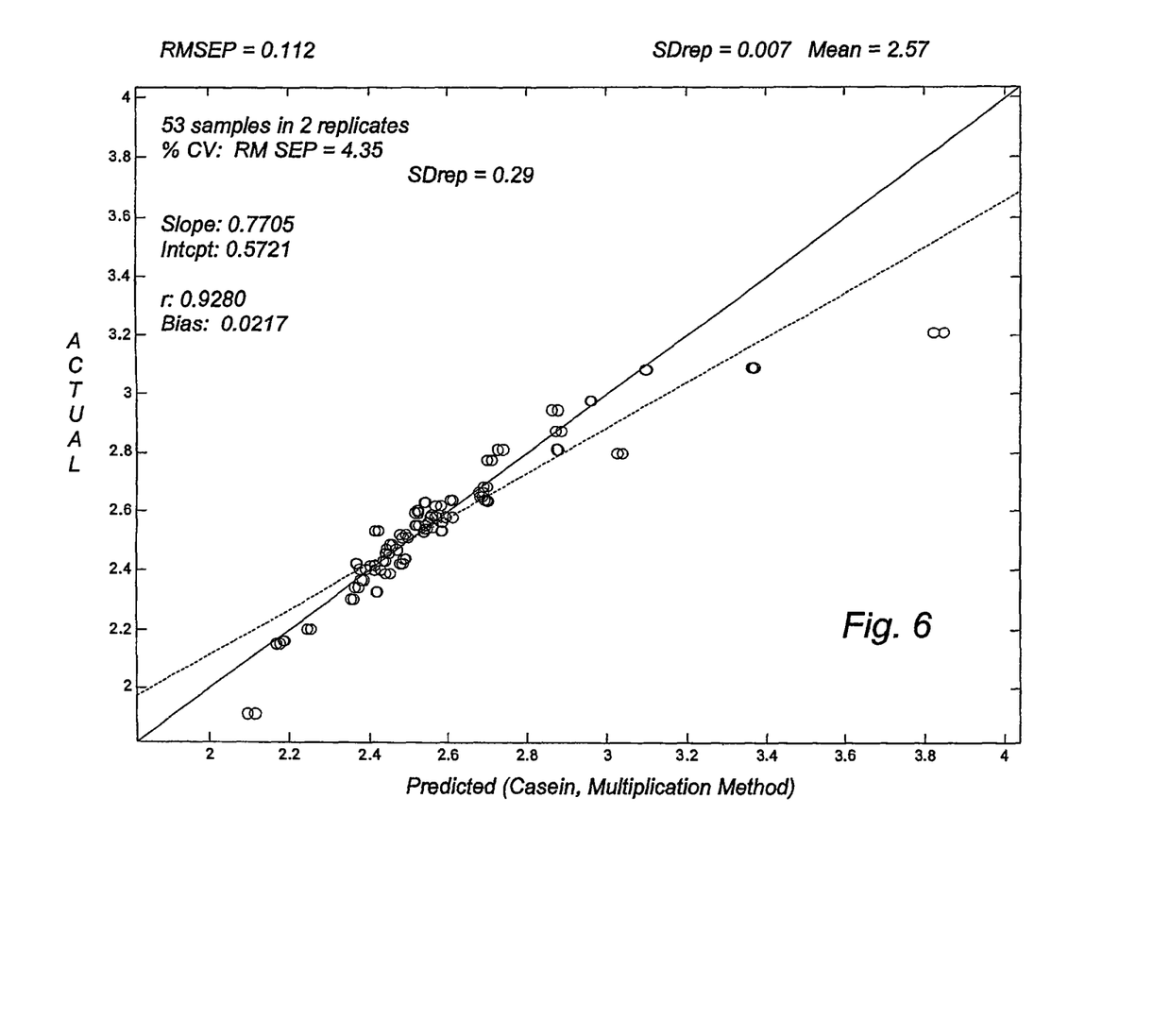
FIG. 6 shows a prediction plot for casein predicted by a known multiplication method.

In FIG. 6: Number of samples: 53 samples in 2 replicates
The obtained absolute accuracy is:
RMSEP=0.112; SDrep=0.007; Mean=2. 57.
The accuracy relative to the mean is: RMSEP=4.35% CV; SDrep=0.29% CV Slope: 0.7705; Intcpt: 0.5721; r: 0.9280; Bias: 0.0217.

By comparison the prediction plots FIGS. 5 and 6 show that the new method determines casein with a relative accuracy (SEPCorr) of 1.39% cv, which is three times as good as the multiplication method (relative accuracy (RMSEP) of 4.35% cv). The multiplication method has special troubles in the high casein concentrations, which makes it more problematic for practical use.

Figure 7:
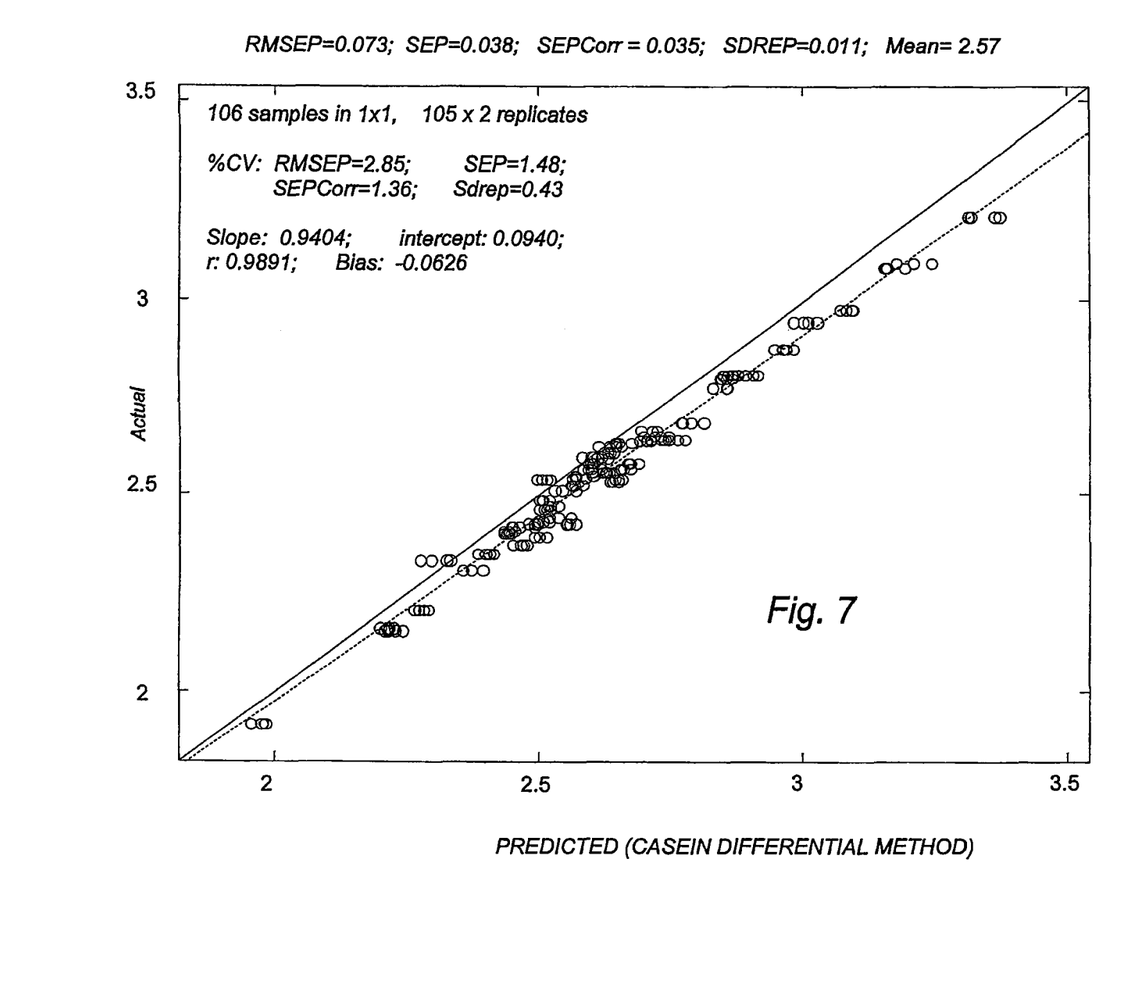
FIG. 7 shows the resulting prediction plot for the differential casein determination using the prediction of the dilution factor.

In FIG. 7 the casein prediction plot is presented for the new method using a predicted dilution factor, i.e. a dilution factor predicted from the absorbance data recorded by the spectrometric analysis instrument.

In FIG. 7: Number of samples: 106 samples in 1×1, 105×2 replicates The obtained absolute accuracy is:
RMSEP=0.073; SEP=0.038; SEPCorr=0.035; SDREP=0.011; Mean=2. 57
The accuracy relative to the mean is
RMSEP=2.85% CV; SEP=1.48% CV; SEPCorr=1.36% CV; SDrep=0.43% CV Slope: 0.9404; intercept: 0.0940; r: 0.9891; Bias: −0.0626

The relative accuracy, SEPCorr, of 1.36% cv is slightly better than the relative accuracy found in the example shown in FIG. 5 for the casein prediction using the weight results, but the slope is slightly lower. This shows that the method incorporating a prediction of the dilution factor will function well in practise.

It is obvious to people skilled in the art that the preferred method according to the invention and as described above may be varied in several ways within the scope of protection as defined in the following patent claims. Other spectrometric instruments than the presently preferred Milkoscan FT120 may be used for carrying out the invention. Other acids able to precipitate the casein might be used, as well as other separation methods.

The invention claimed is:

1. A mid IR spectrometric analysis instrument for determination of the content of casein in milk using a method where a milk sample is measured by infrared spectrometry to provide infrared absorbance data before and after a separation of the sample into a casein and liquid phase, the instrument comprising a computer encoded with a software program configured to direct operation of the spectrometer and execute the following steps:
   a) performing a first measurement by infrared spectrometry to measure infrared absorbance in the milk sample before separation and recording absorbance data obtained by the first measurement
   b) performing a second measurement by infrared spectrometry to measure infrared absorbance in a supernatant and recording absorbance data obtained by the second measurement
   c) calculating a dilution factor indicating the dilution of the supernatant compared to the original milk sample wherein the dilution factor is applied in a calculation of casein concentration, and
   d) calculating the casein content by use of absorbance data recorded during the two infrared spectrometry measurements and the dilution factor.

2. A mid IR spectrometric analysis instrument according to claim 1 characterized in that the instrument comprises a software program configured to execute calculations of the content of casein by use of data enabling a calculation of a dilution factor indicating the dilution of the whey compared to the original milk sample.

3. The mid IR spectrometric analysis instrument according to claim 1 characterised in that the instrument comprises a software program configured to execute a method that is carried out by use of a full spectrum instrument, having a first calibration enabling a calculation of the protein content from the spectrum of the milk and the instrument having a second protein calibration enabling a calculation of the protein content from the spectrum of the supernatant-sample (also called the filtrate).

4. A mid IR spectrometric analysis instrument according to claim 1 wherein the spectrometric instrument comprises a plurality of interchangeable optical IR filters able to be inserted into the light path of the spectrometric instrument.

5. A mid IR spectrometric analysis instrument according to claim 1 wherein the spectrometric instrument is a Full spectrum instrument providing data representing a substantial portion of the MID-IR spectrum.

6. A mid IR spectrometric analysis instrument according to claim 1 wherein the spectrometric instrument provides data representing substantial portions of the MID-IR wavebands wherein proteins absorb.

* * * * *